US009579458B2

(12) United States Patent
Holmqvist (10) Patent No.: US 9,579,458 B2
(45) Date of Patent: Feb. 28, 2017

(54) MEDICAMENT DELIVERY DEVICE

(75) Inventor: Anders Holmqvist, Värmdö (SE)

(73) Assignee: SHL GROUP AB, Nacka Strand (SE)

( * ) Notice: Subject to any disclaimer, the term of this patent is extended or adjusted under 35 U.S.C. 154(b) by 363 days.

(21) Appl. No.: 13/262,638

(22) PCT Filed: Mar. 9, 2010

(86) PCT No.: PCT/EP2010/052930
§ 371 (c)(1),
(2), (4) Date: Oct. 22, 2011

(87) PCT Pub. No.: WO2010/115670
PCT Pub. Date: Oct. 14, 2010

(65) Prior Publication Data
US 2012/0029443 A1 Feb. 2, 2012

Related U.S. Application Data

(60) Provisional application No. 61/166,318, filed on Apr. 3, 2009.

(30) Foreign Application Priority Data

Apr. 3, 2009 (SE) ...................................... 0950216

(51) Int. Cl.
*A61M 5/20* (2006.01)
*A61M 5/24* (2006.01)
*A61M 5/315* (2006.01)

(52) U.S. Cl.
CPC .......... *A61M 5/20* (2013.01); *A61M 5/31536* (2013.01); *A61M 5/2033* (2013.01);
(Continued)

(58) Field of Classification Search
CPC .............. A61M 5/315; A61M 5/31586; A61M 5/31501–2005/3151;
(Continued)

(56) References Cited

U.S. PATENT DOCUMENTS 2,472,116 A * 6/1949 Maynes ........................ 604/136
3,702,609 A * 11/1972 Steiner ................ A61M 5/2033
604/139
(Continued)

FOREIGN PATENT DOCUMENTS

WO 03/053499 A1 7/2003
WO 2004082748 A1 9/2004
(Continued)

OTHER PUBLICATIONS

EPO, Intl Search Report in PCT/EP2010/052930, Jul. 29, 2010.
EPO, Written Opinion in PCT/EP2010/052930, Jul. 29, 2010.

*Primary Examiner* — Imani Hayman
*Assistant Examiner* — Laura Schell
(74) *Attorney, Agent, or Firm* — McDonnell Boehnen Hulbert & Berghoff LLP (57) ABSTRACT

The present invention relates to a medical delivery device comprising a tubular distal housing; a tubular proximal housing; a medicament container arranged inside said tubular proximal housing; a threaded hollow plunger rod; a spring force means pre-tensioned arranged within said plunger rod; activation means arranged to be movable between a non-medicament delivery state and a medicament delivery state; dose setting means being threadedly arranged to said threaded hollow plunger rod and arranged to be rotationally moved between a stop position and a set dose position, whereby upon activation of said activation means from the non-medicament delivery state to the medicament delivery state, said threaded hollow plunger rod is linearly displaced due to the force of the pre-tensioned spring means such that the dose setting means is also linearly displaced from the set dose position to the stop position.

5 Claims, 9 Drawing Sheets

(52) U.S. Cl.
CPC ........... *A61M 5/24* (2013.01); *A61M 5/31505* (2013.01); *A61M 5/31551* (2013.01); *A61M 5/31563* (2013.01); *A61M 5/31591* (2013.01); *A61M 2005/2013* (2013.01)

(58) Field of Classification Search
CPC ...... A61M 5/31525–5/31551; A61M 5/31555; A61M 5/31578; A61M 5/31581
USPC ............................... 604/208, 211, 228, 209
See application file for complete search history.

(56) References Cited

U.S. PATENT DOCUMENTS

| | | | |
|---|---|---|---|
| 3,905,366 A * | 9/1975 | Callahan et al. | ............. 604/209 |
| 2005/0137571 A1 | 6/2005 | Hommann | |
| 2006/0069355 A1* | 3/2006 | Judson et al. | ................ 604/211 |
| 2007/0225656 A1 | 9/2007 | Hoyle, Jr. | |

FOREIGN PATENT DOCUMENTS

| | | | | |
|---|---|---|---|---|
| WO | 2006080893 A1 | | 8/2006 | |
| WO | WO 2006/080893 | * | 8/2006 | ............. A61M 5/20 |
| WO | 2007066152 A1 | | 6/2007 | |
| WO | WO2008/031237 | * | 3/2008 | |

* cited by examiner

MEDICAMENT DELIVERY DEVICE

TECHNICAL AREA

The present invention relates to a medicament delivery device and in particular a device capable of delivering multiple doses of medicament with the same or different dose sizes.

TECHNICAL BACKGROUND

There are on the market a large number of medicament delivery devices such as injectors having a number of different features and/or functions to be able to deliver a certain dose quantity to the user in a safe, reliable and reasonably simple and intuitive manner.

One drawback that many delivery devices suffer from is that the number of components tends to increase dramatically when the number of functions and features are increasing, where the functions could be any or several of mixing, priming, penetration, medicament delivery, withdrawal and covering of the injection needle.

The added complexity regarding the number of components and their interaction in order to perform the desired functions may make it difficult to actually have a reliable functionality without undue precision and tolerance demands and or expensive choice of material, which of course adds to the cost of the medicament delivery device.

Some attempts have been made in order to try to keep the number of components on reasonable levels and yet have a reliable device with a number of functions. The document WO 2005046770 discloses a medicament delivery device arranged with a dose setting drum that is threaded onto a threaded section of a plunger rod for setting a dose. Dose quantity indications are arranged on the dose setting drum. However, in order to obtain an injection operation after a set dose, a number of components are required, for instance for preventing the dose setting drum from rotating relative the plunger rod.

BRIEF DESCRIPTION OF THE INVENTION

The aim of the present invention is to remedy the above mentioned problems and to provide a functional and versatile medicament delivery device that yet is capable of utilizing few components.

This aim is obtained by a medical delivery device according to the independent patent claim. Preferable embodiments of the present invention form the subject of the dependent patent claims.

According to a main aspect of the invention, it is characterised by a medicament delivery device comprising a tubular distal housing having a stop wall and a first distal end wall; a tubular proximal housing having opposing proximal and distal ends; a medicament container arranged inside said tubular proximal housing said medicament container comprising a collar with or for receiving a delivery member, a medicament chamber in which a volume of medicament is enclosed, and an axially slidably and sealably stopper; a threaded hollow plunger rod having a first proximal end wall being in contact with said stopper; a spring force means pre-tensioned arranged within said plunger rod between said first proximal end wall and said first distal end wall; activation means arranged to be movable between a non-medicament delivery state when said activation means are engaged to said threaded hollow plunger rod and a medicament delivery state when said activation means are disengaged from said threaded hollow plunger rod; and dose setting means having a second proximal end and a second distal end, said dose setting means being threadedly arranged to said threaded hollow plunger rod and arranged to be rotationally moved between a stop position when said second proximal end is in contact with the stop wall of said a tubular distal housing and a set dose position when said second proximal end is at a certain distance from the to the stop wall such that said certain distance corresponds to a certain dose; and whereby upon activation of said activation means from the non-medicament delivery state to the medicament delivery state, said threaded hollow plunger rod is linearly displaced due to the force of the pre-tensioned spring means such that the dose setting means is also linearly displaced from the set dose position to the stop position.

There are a number of advantages with the present invention. There is an advantage in many aspects that the dose setting is performed by rotatably displacing a dose setting means along a threaded hollow plunger rod while it is held stationary and that the subsequent medicament delivery is performed by a linear movement of the threaded hollow plunger rod. In this way the number of components needed for both the dose setting and for the medicament delivery operations are reduced in comparison with conventional injectors.

The threaded hollow plunger rod is advantageously used both for holding the plunger rod in the stationary position during dose setting and for setting a dose. According to the second embodiment of the invention, the holding of the plunger rod is obtained by a number of flexible tongues engaging the threaded hollow plunger rod, which tongues can be moved out of engagement by a release button. This solution also reduces the number of components.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The medicament delivery device shown in the drawings comprises:
- a tubular distal housing 11; 112 having a stop wall 16; 160 and a first distal end wall 28; 154;
- a tubular proximal housing 10; 110 having opposing proximal and distal ends;
- a medicament container 12; 114 arranged inside said tubular proximal housing, said medicament container comprising a collar 13;113 with or for receiving a delivery member 18; 118, a medicament chamber in which a volume of medicament is enclosed, and an axially slidably and sealably stopper 20; 130;
- a threaded hollow plunger rod 36; 128 having a first proximal end wall being in contact with said stopper;
- a spring force means 46; 158 pre-tensioned arranged within said plunger rod 36; 128 between said first proximal end wall 28a and said first distal end wall 28; 154;
- activation means 30, 122 arranged to be movable between a non-medicament delivery state when said activation means are engaged to said threaded hollow plunger rod and a medicament delivery state when said activation means are disengaged from said threaded hollow plunger rod; and
- dose setting means 44; 146 having a second proximal end 44a and a second distal end 44b said dose setting means being threadedly arranged to said threaded hollow plunger rod 36; 128 and arranged to be rotationally moved between a stop position when said second proximal end 44b is in contact with the stop wall 16 of said tubular distal housing 11; . . . 112 and a set dose position when said second proximal end is at a certain distance from the to the stop wall such that said certain distance corresponds to a certain dose; and whereby upon activation of said activation means from the non-medicament delivery state to the medicament delivery state, said threaded hollow plunger rod is linearly displaced due to the force of the pre-tensioned spring means such that the dose setting means is also linearly displaced from the set dose position to the stop position.

The proximal end of the tubular proximal housing 10; 110 is arranged with an opening 14; 114 on a neck 16; 116, onto which the delivery member, such as a needle18; 118 may be attached e.g. by threads. It is however to be understood that other medicament delivery members such as nozzles, mouthpieces etc. may be utilised within the present invention. Moreover, the tubular proximal housing 10; 110 is arranged with longitudinal openings or windows 15; 115.

The tubular distal housing 11 comprises a first distal part 22 having at least one longitudinally extending slit 24, and said threaded hollow plunger rod comprises at least one distal threaded ridge 38 arranged longitudinally movable into the at least one slit 24. Moreover, the first distal part 22 is arranged with external threads 26 on its distal end, FIG. 3.

Figure 3:
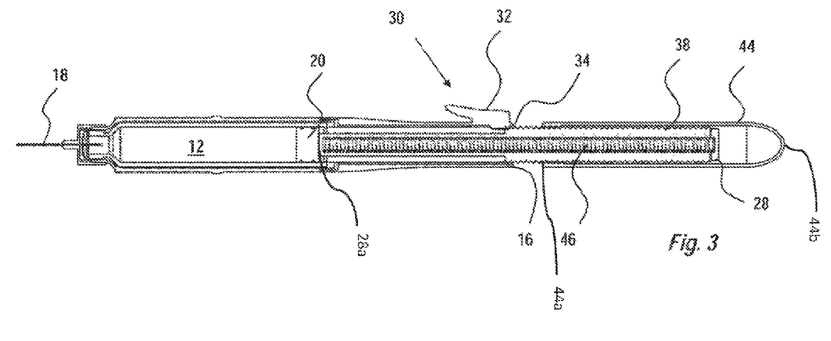
FIG. 3 is a side view in cross-section of the embodiment of FIG. 1.

The dose setting means 44 is a tubular sleeve threadedly arranged to the at least one distal threaded ridge 38, FIG. 3.

Figure 2:
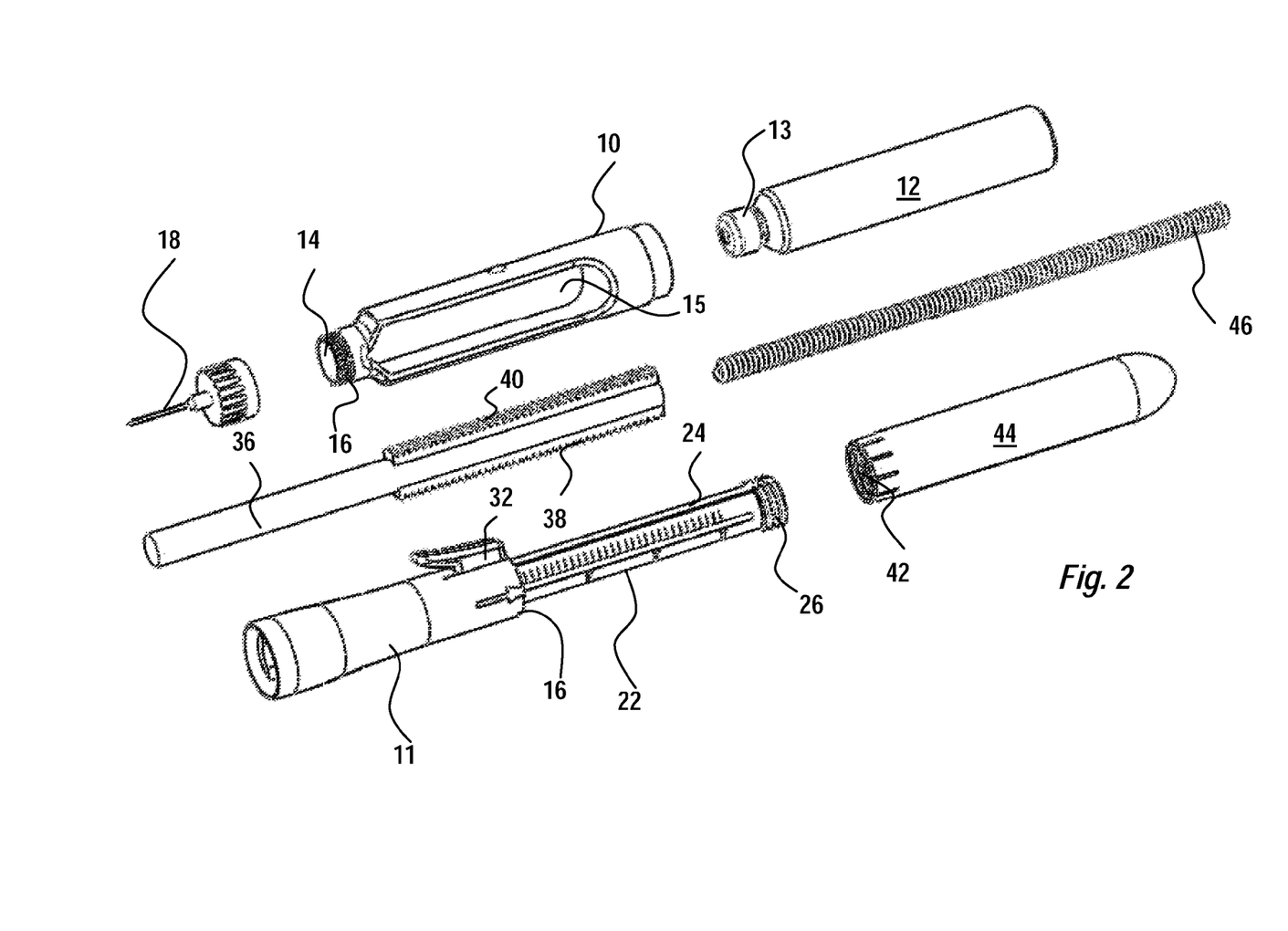
FIG. 2 is an exploded view of the embodiment of FIG. 1.

The at least one distal threaded ridge 38 of the threaded hollow plunger rod 36 is further arranged with threads 40 on their upper surface, FIG. 2. These threads 40 mate both with the external threads 26 on the distal end of the first distal part 22 and with internal threads 42 on the inner surface of the dose setting means 44, hereafter named dose setting knob, FIG. 2.

The activation means 30 comprises a release button 32 arranged extending through an opening in the tubular distal housing just in front of the first distal part 22. The release button 32 has a lock member 34 engageable with the threads 40 of the threaded hollow plunger rod, which lock member is moved out of contact with the threads 40 of the threaded hollow plunger rod upon activation of said release button, FIG. 3.

The device is intended to function as follows. When the device is delivered to a user, the threaded hollow plunger rod is positioned in its distalmost position, whereby its threads 40 mate with the external threads 26 on the distal end of the first distal part 22. This design is to ensure a positive and stable initial connection when the dose setting knob is threaded onto the tubular part.

Figure 1:
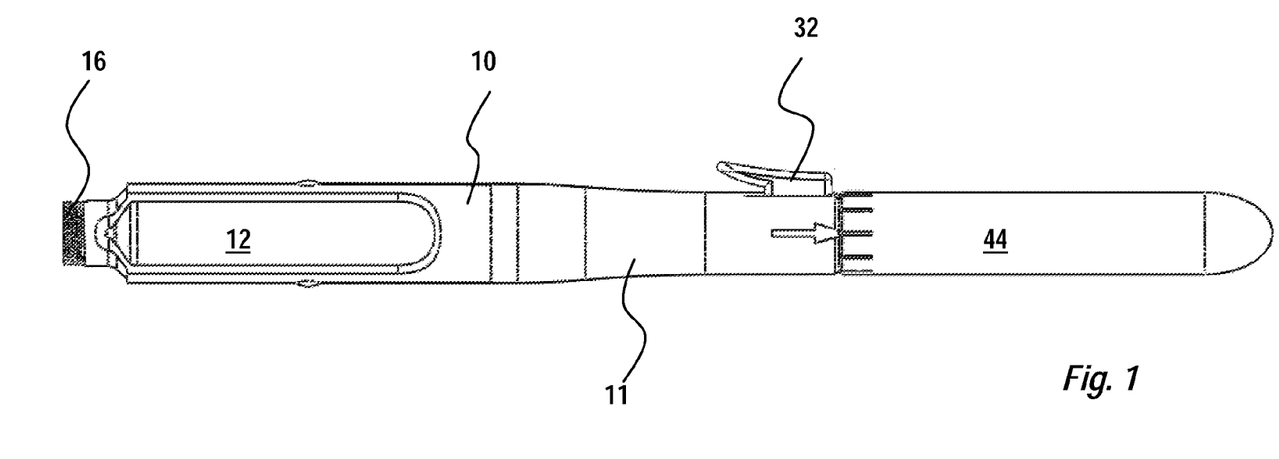
FIG. 1 is a side view of a first embodiment of the present invention.

When a user is to take a dose of medicament, a medicament container 12 is placed inside the tubular proximal housing 10. The tubular proximal housing 10 is then connected to the tubular distal housing 11, FIGS. 1 and 2. The dose setting knob 44 is then rotated clockwise until the first proximal end wall of the threaded hollow plunger rod 36 makes in contact with the stopper, during which operation the release button is in a medicament delivery state in order to allow the forward movement of the plunger rod due to the force of the spring force means. The contact point is then set as the start or reference position. The release button 32 is then released to a non-medicament delivery state whereby the threaded hollow plunger rod is locked in this axial position. The user now sets the desired and prescribed dose by turning the dose setting knob 44. Due to the interaction between the internal threads 42 of the dose setting knob and the threads 40 of the ridges of the threaded hollow plunger rod the dose setting knob is moved in relation to the first distal part 22 from its stop position to its set dose position. The dose setting knob 44 is turned until the prescribed dose is set, as can be indicated by suitable indicia on the first distal part 22 co-acting with indicators on the dose setting knob. After this, in the case of an injector, a needle is attached to the neck 16 of the tubular proximal housing 10.

The patient then positions the delivery member at the intended medicament delivery site, in the case of an injector penetrating the skin with the needle, and activates the activation mechanism 30 from the non-medicament delivery state to the medicament delivery state, whereby the lock member 34 moves out of contact with the threads 40 of the threaded hollow plunger rod 36, such that the threaded hollow plunger rod becomes free to move linearly towards the proximal end of the device due to the force of the spring force means 46, which in turn causes the stopper 20 to move towards the proximal end of the device, whereby the set dose of medicament is expelled through the delivery member. The medicament delivery terminates when the second proximal end of the dose setting knob makes contact with the stop wall of said a tubular distal housing 11, wherein said stop wall is an annular ledge of said tubular distal housing. The medicament delivery device is now ready to be removed from the medicament delivery site.

Figure 4:
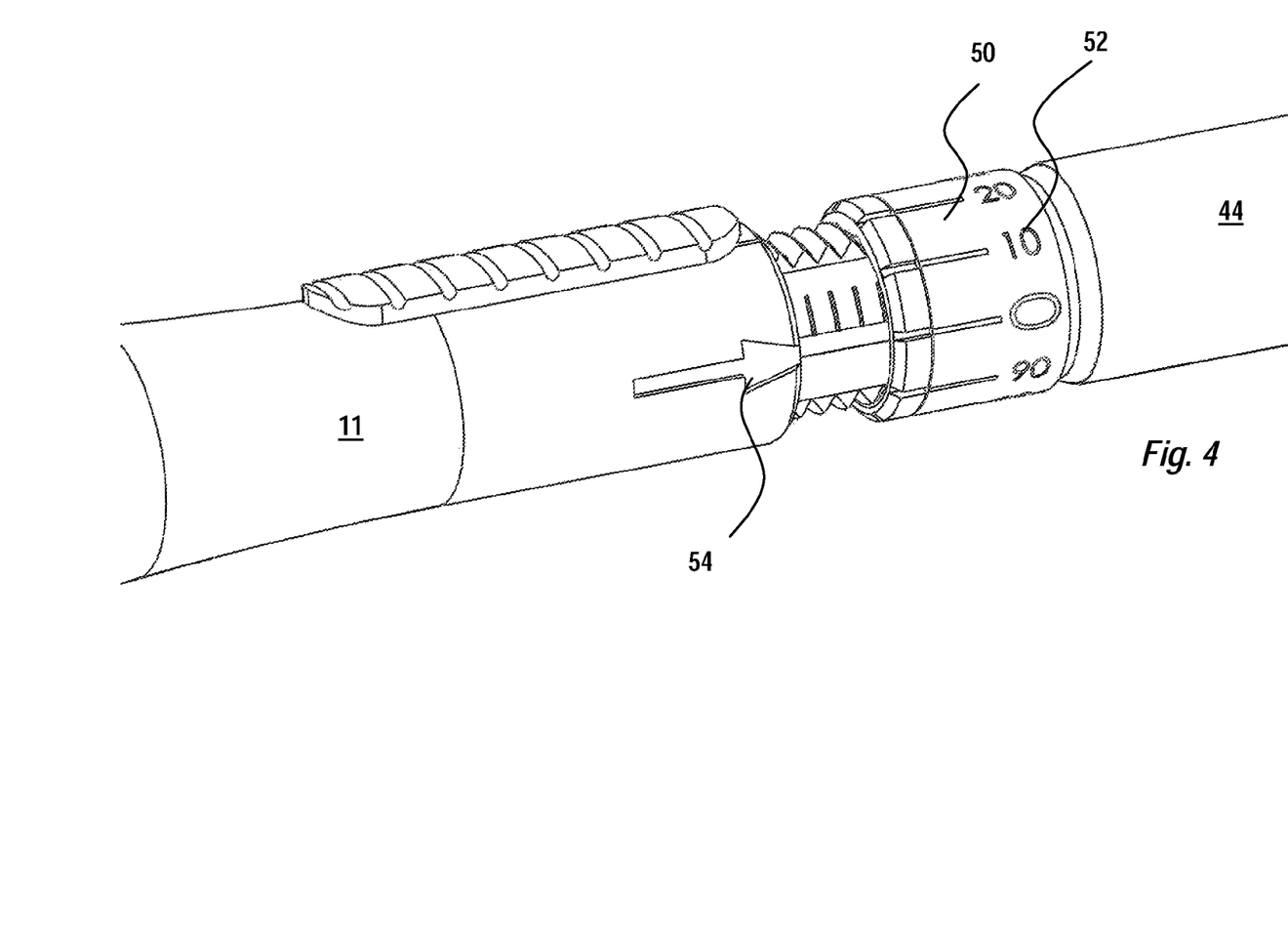
FIG. 4 is a detailed view of a modification of the embodiment of FIG. 1.

A modification of the first embodiment is shown in FIG. 4 where a resettable dose indicator 50 is shown. The resettable dose indicator 50 is a tubular sleeve comprising dose indications 52 around its outer circumference surface and comprises a distal end and a proximal end. The resettable dose indicator 50 is arranged around the first distal part 22 having a first axial position where it is rotationally locked with the dose setting knob and a second axial position where it is rotationally released from the dose setting knob. When the dose setting knob 44 is turned, so is the resettable dose indicator 50 until the prescribed dose indication 52 is aligned with a reference indication 54 on the tubular distal housing 11 as shown in FIG. 4.

When a dose is subsequently delivered, the threaded hollow plunger rod and the dose setting knob are linearly moved together towards the proximal end of the device due to the force of the spring force means until the proximal end of the resettable dose indicator comes in contact with the stop wall of said a tubular distal housing 11.

Due to the linear movement of the threaded hollow plunger rod, the resettable dose indicator will now indicate the previously set dose even though a dose has not yet been set. In order to reset the dose indicator, it is moved axially in relation to the dose setting knob to the second axial position where it becomes free to rotate in relation to the dose setting knob. Thus, the user rotates the resettable dose indicator until it is put back to the first axial position.

Figure 5:
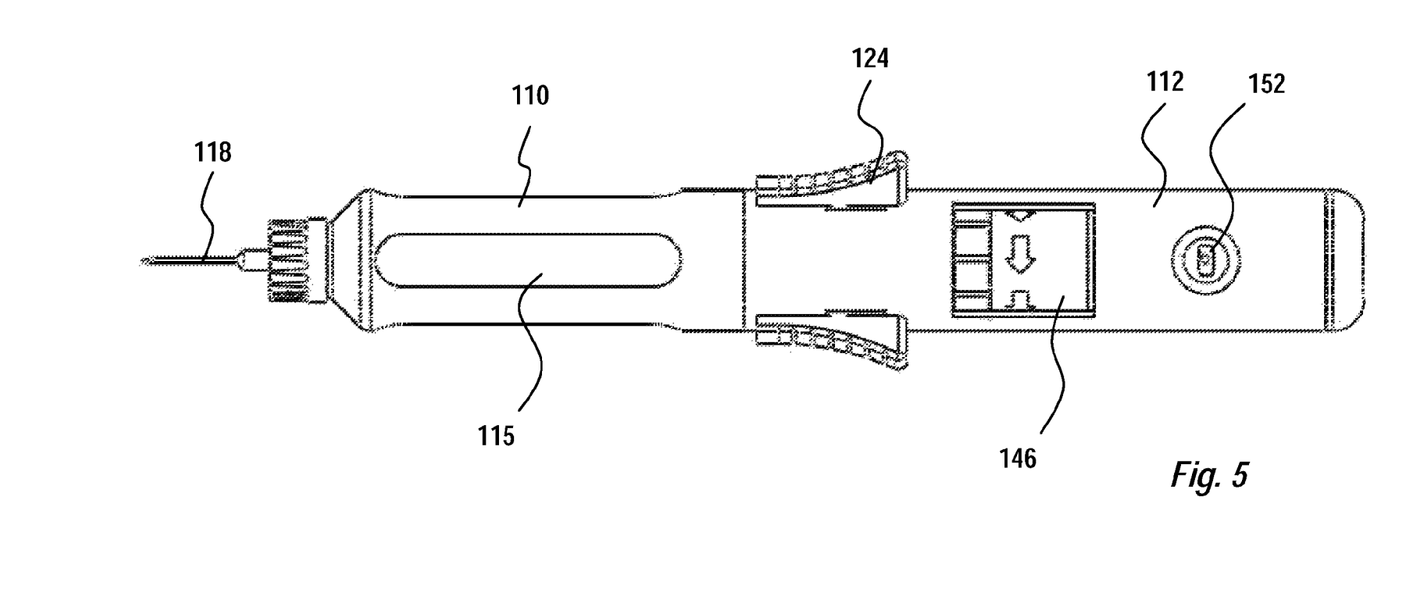
FIG. 5 is a side view of a second embodiment of the present invention.
Figure 6:
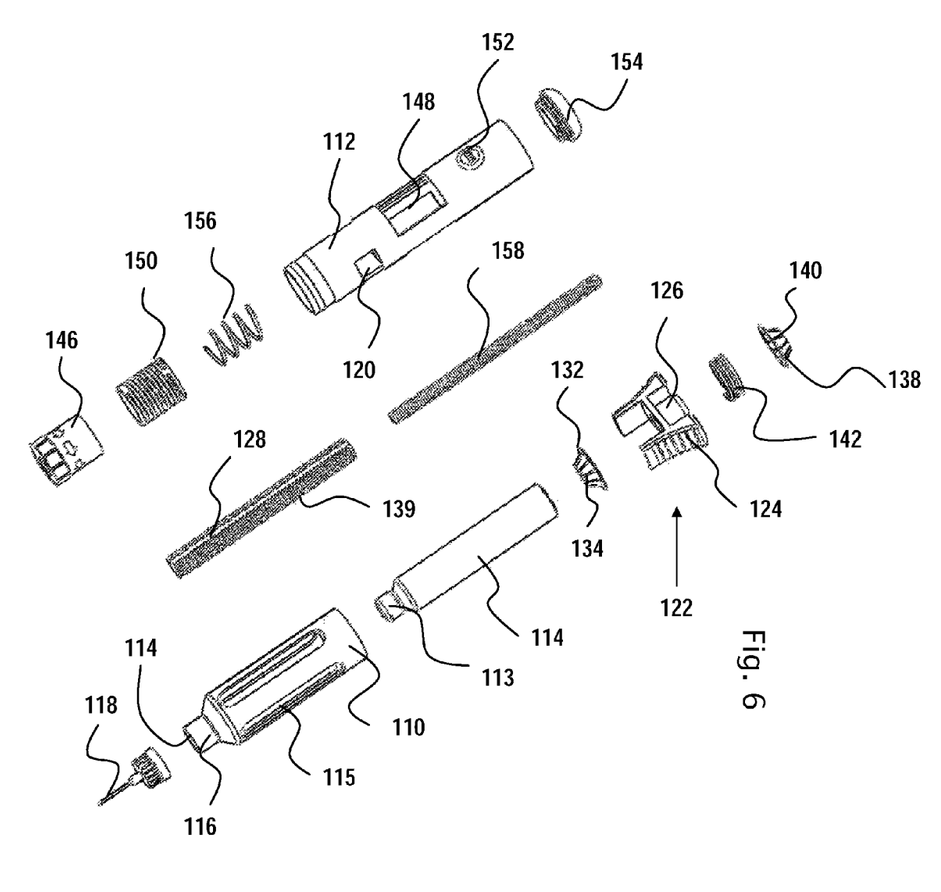
FIG. 6 is an exploded view of the embodiment of FIG. 5.
Figure 7:
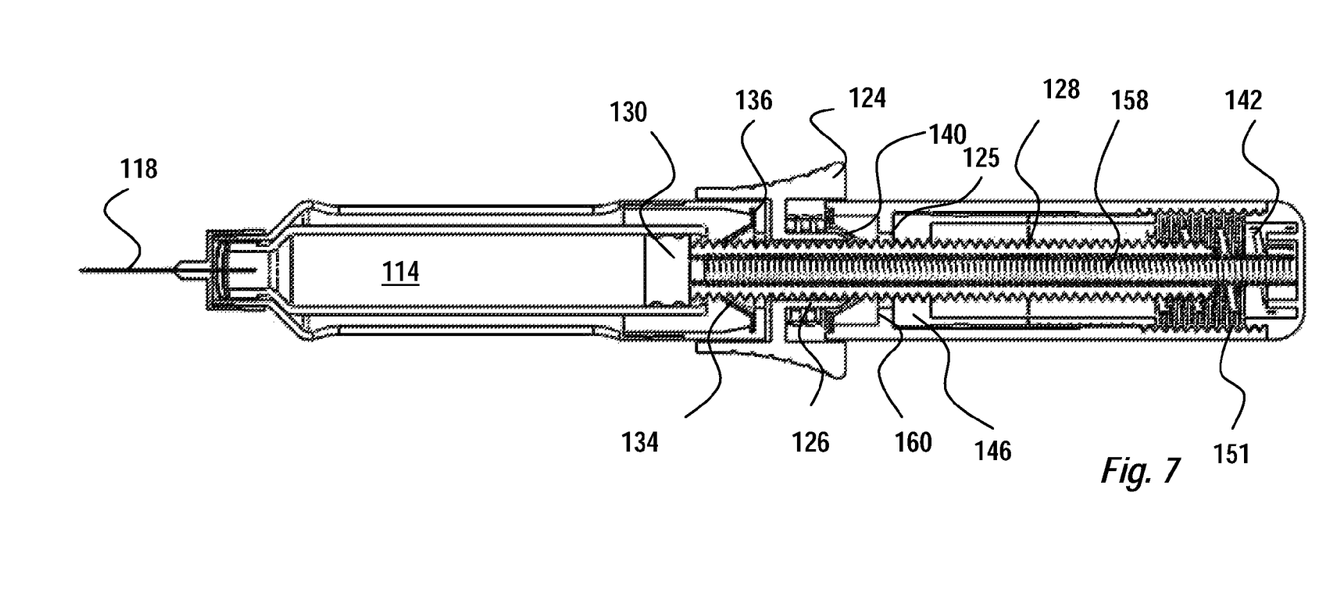
FIG. 7 is a side view in cross-section of the embodiment of FIG. 5.

FIGS. 5 to 7 show another embodiment of the present invention. The tubular distal housing 112 is arranged with a number of openings and on the inner surface of the tubular distal housing 112 the stop wall 160 is arranged having at least one longitudinally extending slit 125. The threaded hollow plunger rod 128 comprises at least one threaded ridge 139 arranged longitudinally movable into the at least one slit 125.

The dose setting means 146 is a dose setting drum being threadedly arranged around the at least one threaded ridge 139, and being accessible via at least one first opening 148 on said tubular distal housing 112.

As seen in FIG. 6, the activation means 122 comprises:
a ring shaped sleeve 126 having at least one button 124 protruding through at least one second opening 120 on said tubular distal housing 112, wherein said ring shaped sleeve is arranged around and slidable along the threaded hollow plunger rod 128;
a first ring 138 surrounding the threaded hollow plunger rod and having a number of flexible tongues 140 engageable with the at least one threaded ridge 139 of the threaded hollow plunger rod, wherein said first ring may be integrated or fixedly attached to the inner surface of the tubular distal housing; and
a spring 142 arranged between the ring shaped sleeve and the first ring.

Further, a second ring 132 having a number of inclined flexible tongues 134 is arranged in contact with an inner central wall 136 on the inner surface of the tubular distal housing 112, through which the threaded hollow plunger rod 128 extends, as seen in FIG. 7, and wherein said second ring may be integrated or fixedly attached to said inner central wall. The ends of the inclined flexible tongues 134 are in contact with the at least one threaded ridge 139 of the threaded hollow plunger rod for preventing the plunger rod from moving in towards the distal end of the device.

A dose indication drum 150 is threadedly interconnected to said tubular distal housing 112 by internal threads 151 on the inner surface of said tubular distal housing 112. Said dose indication drum is also releasibly connected to the dose setting drum 146. The dose indication drum is engaged to the dose setting drum when the dose setting drum is moved from its stop position to its set dose position for displaying a set dose with a dose indication from a set of dose indications, such as dose quantities, on the outer surface of said dose indication drum through a window 152 on the tubular distal housing 112. The dose indication drum is disengaged from said dose setting drum when the dose setting drum is moved from its set dose position to its stop position.

The first distal end wall 154 may be integrated or attached to the distal end of the tubular distal housing 112 housing. A torsion spring 156 is arranged having one end connected to the tubular distal housing 112 and the other end connected to the dose indication drum 150 for rotating the dose indication drum when it is disengaged from the dose setting drum and thereby resetting said dose indication.

The embodiment is intended to function as follows. A medicament container 114 is inserted into the tubular proximal housing 110 and the two housing parts 110, 112 are connected to each other. A medicament delivery member 118 is attached to the neck 116 of the tubular proximal housing 110. The user now has to set a dose of medicament to be delivered. This is done by rotating the dose setting drum 146 through the first opening 148. The rotation causes the dose setting 146 drum to be rotatably displaced towards the distal end of the device along the threaded hollow plunger rod 128 due to the threaded connection. The second proximal end of the dose setting drum 146 is thus moved out of contact from the stop wall 160 of the tubular distal housing, FIG. 7. The connection between the dose setting drum 146 and the dose indication drum 150 causes the latter to rotate as well, displaying dose quantities in the window 152. Thus, the user rotates the dose setting drum 146 until the proper dose is indicated in the window. When the dose indication drum 150 is rotated it is displaced towards the distal end of the device due to the threaded connection between the dose indication drum and the threads 151 on the tubular distal housing. Further, the rotation of the dose indication drum 150 causes the torsion spring 156 to be tensioned.

The user then positions the delivery member at the intended medicament delivery site, in the case of an injector penetrating the skin with the needle, after which the at least one button 124 can be activated. This is done by sliding the at least one button 124 towards the distal end of the device against the force of the spring 142. This causes the ring shaped sleeve 126 to act on the tongues 140 of the first ring such that they move out of contact with the at least one threaded ridge 139 of the threaded hollow plunger rod. The threaded hollow plunger rod is then free to move linearly towards the proximal end of the device due to the force of the spring force means, whereby the stopper also is moved and the set dose of medicament is expelled through the delivery member. The delivery is stopped when the second proximal end of the dose setting drum, which moves together with the threaded hollow plunger rod, comes into contact with the stop wall 160 of the tubular distal housing. The torsion spring now causes the dose indication drum to rotate back to its original position. When the at least one button 124 is released, the ring shaped sleeve 126 is moved back to its original position by the spring 142, whereby the tongues 140 of the first ring are free to flex inwards and move into contact with the at least one threaded ridge 139 of the threaded plunger rod again.

Figure 8:
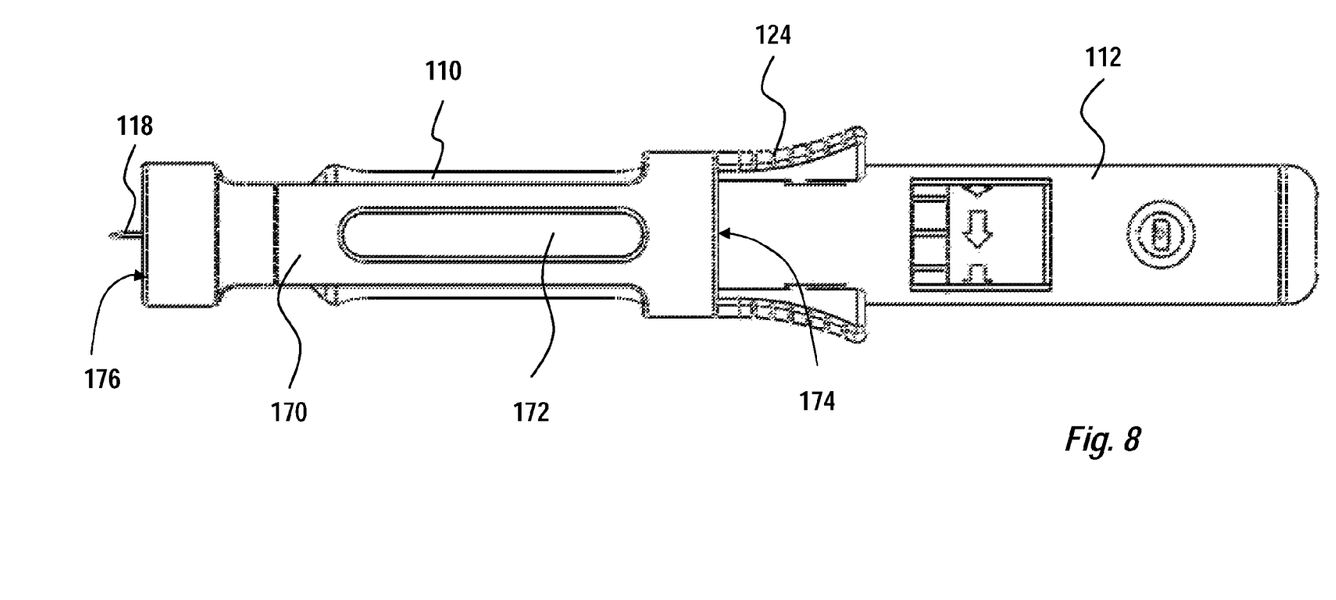
FIG. 8 is a side view of the embodiment of FIG. 5 added with an auto-injection function.

FIG. 8 shows an added function to the embodiment described in FIGS. 5-7. It is easy to add an auto-injection function to that embodiment. Here a combined needle shield actuator 170 having a distal edge 174 and a proximal edge 176 is provided. It is designed as a generally tubular body arranged with an inner diameter that is somewhat smaller than the tubular proximal housing 110 of the device, such that the needle shield actuator 170 is slidable in relation to the housing. The needle shield actuator is arranged with openings or windows 172 corresponding to the openings 115 of the tubular proximal housing 110. The length of the actuator 170 is preferably such that when placed on the tubular proximal housing 110, the distal edge 174 of the needle shield actuator 170 is in contact with the at least one button 124 and the proximal edge 176 of the needle shield actuator 170 is generally in the same plane as the proximal tip of the injection needle 118. When a user wants to utilize the auto-injection function, the of the needle shield actuator 170 is slid onto the tubular proximal housing 110. The proximal edge 176 of the needle shield actuator 170 is then pressed against an injection site whereby a penetration is performed during movement of the needle shield actuator 170 in the distal direction. When a certain penetration depth has been reached, i.e. the needle shield actuator 170 has moved a certain distance in relation to the housing, the at least one button 124 has been moved in the distal direction due to the contact between the distal edge 174 of the needle shield actuator 170 and the proximal edge of the at least one button 124 such that an injection is activated as described above.

In this context there is preferably some kind of contact between the needle shield actuator 170 and the tubular proximal housing 110 so that the needle shield actuator stays in place if the device is positioned vertically with the needle shield actuator pointing downwards. However the contact preferably is such that the force for providing movement between the needle shield actuator and the tubular proximal housing is not too high.

For example there could be a circumferential protrusion on the outer surface of the tubular proximal housing 110 and a corresponding protrusion on the inner circumferential surface of the needle shield actuator 170 such that when the needle shield actuator has been pushed onto the tubular proximal housing, the protrusions are forced over each other for allowing further movement in the distal direction but preventing the needle shield actuator to move in the proximal direction more than to the contact point of the protrusions. Also the tubular proximal housing could be provided with two circumferential protrusions and that the circumferential protrusion of the needle shield actuator is moved past both of the protrusions of the tubular proximal housing for penetration and injection. When the device is removed from the injection site, the needle shield actuator is moved manually in the proximal direction until the circumferential protrusion of the needle shield actuator is positioned between the protrusions of the tubular proximal housing, whereby the needle shield actuator is prevented from moving in any direction, thereby preventing unintentional needle sticks.

Further, resilient means (not shown) may be arranged within said needle shield actuator, such that when the device is removed from the injection site, the needle shield actuator will be forced towards the proximal end of the device for covering the needle.

Figure 9:
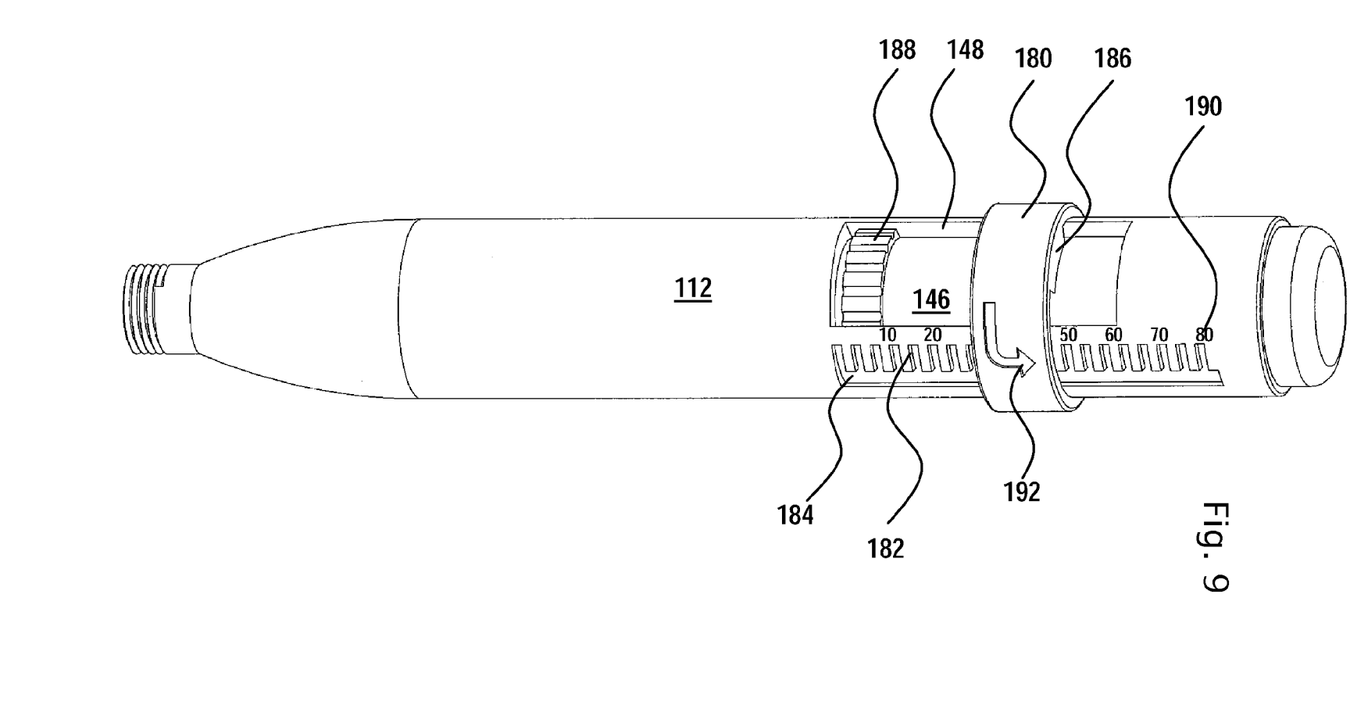
FIG. 9 is a variant of the embodiment of FIG. 5 with a dose limiting member.

FIG. 9 shows a further added functional feature of the present invention. Here the device is provided with a maximum dose limiting member 180. This maximum dose limiting member comprises a ring-shaped member arranged releasebly and slidable around the tubular distal housing 112. Further a number of transversally arranged grooves 182 are positioned adjacent the at least one first opening 148 on said tubular distal housing 112. The transversal grooves 182 are interconnected by a longitudinally extending groove 184 on said tubular distal housing 112. The ring 180 is further arranged with a radially directed protrusion (not shown) co-operating with the grooves 182, 184 as will be explained. Further the inner surface of the ring 180 is provided with a radially directed ledge 186. This ledge cooperates with circumferentially extending ledge 188 of the dose drum 146.

When a certain maximum dose is to be set the ring 180 is turned such that the radially directed protrusion is positioned in the longitudinal groove 184, thereby enabling a longitudinal sliding of the ring. The ring is thus moved until it is positioned corresponding to the prescribed maximum dose to be delivered. This may be indicated by indicia 190 on the outer surface of the tubular distal housing 112 and an indication 192 on the ring or by the side edge of the ring 180. When the proper position is reached, the ring is turned whereby the inwardly directed protrusion is positioned in one of transversal grooves 182, corresponding to the dose. When the dose then is to be set, the dose drum 146 is rotated manually by the user's finger acting on the circumferentially extending ledge 188 of the dose drum 146. Said rotation causes the circumferentially extending ledge 188 to move in the distal direction until it comes in contact with the ledge 186 of the ring 180. It is thus not possible to move the dose drum any further.

It is to be understood that the max dose limiting member 180 may be locked by a locking member more permanently after the prescribed max dose has been set, in order to make it difficult to change the max dose, which is of particular importance when for example children are to use the device. The locking member could comprise a pin or a screw that is forced through passages in the ring as well as the housing and held in position by friction or by threads respectively, which locking members are difficult to remove without tools.

It is to be understood that the embodiment described above and shown in the drawings is to be regarded only as a non-limiting example of the present invention and that it may be amended in many ways within the scope of the patent claims.

The invention claimed is:

1. A medicament delivery device, comprising:
   a tubular distal outer housing having a stop wall on the tubular distal outer housing;
   a tubular proximal housing having opposing proximal and distal ends;
   a medicament container arranged inside the tubular proximal housing and comprising a collar configured for a delivery member, a medicament chamber in which a volume of medicament is enclosed, and an axially slidable and sealable stopper;
   a hollow plunger rod having an outer surface containing at least one distal threaded ridge extending longitudinally along the hollow plunger rod and arranged with threads configured to mate with internal threads on a dose setting knob, where the hollow plunger rod has a first proximal end wall configured to move inside the medicament container and being in direct contact with the stopper;
   a spring arranged within the hollow plunger rod between the first proximal end wall and a first distal end wall;
   an activation mechanism comprising a lock member having a threaded surface that matches the threads on the at least one distal threaded ridge and movably arranged between a non-medicament delivery state when the activation mechanism is directly engaged to the threads of the at least one distal threaded ridge of the hollow plunger rod and a medicament delivery state when the activation mechanism is disengaged from the threads; and
   where the dose setting knob is a tubular outer sleeve having an open second proximal end and a closed second distal end configured to be directly grasped and rotated by a user, being threadedly engaged to the threads of the hollow plunger rod and arranged to be rotationally and linearly moved in a distal direction during dose setting between a stop position when the second proximal end is in contact with the stop wall of the tubular distal outer housing preventing proximal linear movement of the dose setting knob and the hollow plunger rod and a set dose position when the second proximal end is at a certain axial distance from the stop wall, such that the certain axial distance corresponds to a certain dose;

whereby upon activation of the activation mechanism from the non-medicament delivery state to the medicament delivery state, the hollow plunger rod is linearly displaced due to the spring such that the dose setting knob is also linearly displaced in a proximal direction from the set dose position by the threaded engagement with the hollow plunger rod to the stop position where contact of the second proximal end with the stop wall prevents further linear proximal movement of the hollow plunger.

2. The medicament delivery device of claim 1, wherein the tubular distal housing comprises a first distal part having at least one longitudinally extending slit configured to allow the threads of the threaded hollow plunger rod to project radially outward through the slit and to move longitudinally within the slit.

3. The medicament delivery device according to claim 2, wherein the tubular sleeve has internal threads on the second proximal end that are configured to engage the threads on the threaded ridge.

4. The medicament delivery device according of claim 2, further comprising a resettable dose indicator arranged around the first distal part, wherein the resettable dose indicator has a first axial position where it is rotationally locked with the dose setting knob and a second axial position where it is rotationally released from the dose setting knob, and comprises dose indications around its outer circumference surface.

5. The medicament delivery device of claim 1, wherein the activation mechanism comprises a release button extending through an opening in the tubular distal housing in front of a first distal part, the release button having a lock member configured for engaging the at least one distal threaded ridge of the threaded hollow plunger rod, which lock member is moved out of contact with the at least one distal threaded ridge of the plunger rod upon activation of the release button.

* * * * *